United States Patent [19]

Knifton

[11] 4,334,092
[45] * Jun. 8, 1982

[54] METHOD OF PREPARING ALIPHATIC CARBOXYLIC ACIDS

[75] Inventor: John F. Knifton, Austin, Tex.

[73] Assignee: Texaco Inc., White Plains, N.Y.

[*] Notice: The portion of the term of this patent subsequent to Apr. 7, 1998, has been disclaimed.

[21] Appl. No.: 164,632

[22] Filed: Jun. 30, 1980

[51] Int. Cl.³ ............................................. C07C 51/12
[52] U.S. Cl. .................................... 562/517; 260/399; 260/404; 260/408; 260/413; 260/465.4; 560/265; 562/519
[58] Field of Search ........................ 562/517, 406, 497; 260/465.4, 413, 408, 404, 399

[56] References Cited

U.S. PATENT DOCUMENTS

| | | | |
|---|---|---|---|
| 3,769,329 | 10/1973 | Paulik et al. | 562/517 |
| 4,111,837 | 9/1978 | Taylor | 568/902 |
| 4,189,441 | 2/1980 | Braca et al. | 562/517 |
| 4,260,820 | 4/1981 | Knifton | 562/517 |

Primary Examiner—Vivian Garner
Attorney, Agent, or Firm—Carl G. Ries; Robert A. Kulason; Walter D. Hunter

[57] ABSTRACT

This invention pertains to the production of higher homologues of aliphatic carboxylic acids by reaction of said acids with carbon monoxide and hydrogen in the presence of one or more rhodium-containing catalysts and an iodide or bromide promoter.

14 Claims, No Drawings

METHOD OF PREPARING ALIPHATIC CARBOXYLIC ACIDS

BACKGROUND OF THE INVENTION

1. Field of the Invention

This invention concerns a process for the preparation of carboxylic acids by synthesis gas homologation of aliphatic carboxylic acids using a specific catalyst system.

2. Description of the Prior Art

There is an ever increasing need for a wide variety of aliphatic carboxylic acids of differing carbon numbers and structures which have become important present articles of commerce. The many processes leading to the preparation of these acids include oxidation of saturated and unsaturated hydrocarbons, the carboxylation of monoolefins, particularly α-olefins, and dienes such as conjugated dienes like 1,3-butadiene, and the carbonylation of lower aliphatic alcohols.

We now disclose a new preparative route to short-chain aliphatic acids involving the homologation of lower molecular weight aliphatic carboxylic acids. Homologation is effected by treatment of said carboxylic acids with synthesis gas (a mixture of carbon monoxide and hydrogen).

The homologation of carboxylic acids by means of synthesis gas in the presence of the specific catalyst system of this invention has not, to our knowledge, been disclosed previously. However, in co-pending application Ser. No. 77,970, filed Sept. 24, 1979, now U.S. Pat. No. 4,260,820, the homologation of these same acids by means of synthesis gas and in the presence of a ruthenium-containing catalyst and an iodide or bromide promoter has been set out. The homologation of saturated alkyl benzyl alcohols, and substituted benzyl alcohols, by synthesis gas to yield the corresponding higher molecular weight alcohols has been extensively studied. Pertinent examples include the homologation of methanol to ethanol, and the conversion of ethanol to propanol, butanol and pentanol isomers (see: "Carbon Monoxide in Organic Synthesis" by J. Falbe, pages 59–62 and I. Wender, Catal. Rev. Sci. Eng., 14, 97–129 (1976)). Cobalt carbonyls, with or without phosphine or metal modifiers, are commonly used as catalysts in such alcohol homologation reactions (see: L. N. Slaugh, Ger. Offn. No. 2,625,627 and P. D. Taylor, U.S. Pat. No. 4,111,837).

Related homogeneous cobalt carbonyl catalysts are also effective for the synthesis of aliphatic carboxylic acid via the carbonylation of the lower aliphatic alcohols. More recently, soluble rhodium catalysts have become the catalysts of choice in, for example, the synthesis of acetic acid via methanol carbonylation (Chem. Tech., p. 605, October 1971).

Other relevant homologation technology includes the recently reported homologation of dimethyl ether and methyl acetate to ethyl acetate (see: G. Braca et. al. 9, Amer. Chem. Soc., 100, 6238 (1978)).

One of the objects of this invention is to provide a novel process of homologation of short-chain aliphatic carboxylic acids to the higher homologues thereof by means of a unique catalyst system. The feedstock utilized in this process comprises synthesis gas along with the acid which is homologized.

SUMMARY OF THE INVENTION

In this invention the higher homologues of carboxylic acids are prepared by reaction of said acids with synthesis gas in the presence of one or more rhodium-containing catalysts and a bromide or iodide promoter.

The process of this invention is particularly characterized by the homologation of acetic acid to higher acids according to equation 1 which is illustrative of this process:

$$CH_3COOH + CO/H_2 \rightarrow C_nH_{2n+1}COOH \tag{1}$$

Other lower aliphatic acids such as propionic acid and others containing 2–6 inclusive carbon atoms may also be homologized by a similar procedure.

A high degree of selectivity is exhibited by the reaction of this invention. For example, when acetic acid is converted to $C_2^+$ acids by this process, selectivities of as high as 85% based on acetic acid converted have been achieved.

DETAILED DESCRIPTION OF THE INVENTION

The process of this invention which involves preparing higher homologues of aliphatic carboxylic acids containing 2–6 carbon atoms comprises the steps of contacting the aliphatic acid starting materials with at least a catalytic amount of a rhodium-containing compound in the presence of an iodide or bromide promoter and heating the resultant reaction mixture under pressures of 500 psi or greater with carbon monoxide and hydrogen until substantial formation of the desired acids containing at least 3 carbon atoms has been achieved, and recovering said desired acids.

In carrying out the homogolation reaction of this invention selectively to produce the higher homologues of the charged aliphatic carboxylic acids, it is necessary to supply sufficient carbon monoxide and hydrogen to at least satisfy the stoichiometry of the desired higher carboxylic acid homologues although excess carbon monoxide or hydrogen over the stoichiometric amounts may be present.

It has been found that the homologation reaction is effected only with a synthesis gas mixture, and carbon monoxide alone is not sufficient (contrary to prior art processes involving carbonylation of lower aliphatic alcohols to carboxylic acids).

In addition, it has been found here that an iodide or bromide promoter is necessary for acid homologation to take place according to the general scheme outlined above. Lastly, and surprisingly, it has been found that lower alkyl organic iodide or bromide promoters are much more effective than alkali metal iodides or bromides such as cesium iodide.

The following discloses in greater detail the process of invention.

Catalysts that are suitable for use in the practice of this invention contain rhodium. The rhodium-containing catalyst may be chosen from a wide variety of organic or inorganic compounds, complexes, etc., as will be shown and illustrated below. It is only necessary that the catalyst precursor actually employed contain said metal in any of its ionic states. The actual catalytically active species is then believed to comprise rhodium in complex combination with carbon monoxide and hydrogen. The most effective catalyst is achieved where the rhodium hydrocarbonyl species is solubilized in the carboxylic acid co-reactant employed to satisfy the stoichiometry of eq. 1.

The rhodium catalyst precursors may take many different forms. For instance, the rhodium may be added to the reaction mixture in an oxide form, as in the case of, for example, rhodium(III) oxide hydrate ($Rh_2O_3 \cdot 5H_2O$), rhodium (IV) dioxide ($RhO_2$) and rhodium sesquioxide ($Rh_2O_3$). Alternatively, it may be added as the salt of a mineral acid, as in the case of rhodium(III) chloride hydrate, rhodium (III) bromide, rhodium (III) iodide, chlorodicarbonyl rhodium (I) dimer, anhydrous rhodium(III) chloride and rhodium nitrate, or as the salt of a suitable organic carboxylic acid, for example, rhodium(II) formate, rhodium(II) acetate, rhodium(II) propionate, rhodium(II) butyrate, rhodium(II) valerate, rhodium(III) napththenate, etc. The rhodium may also be added to the reaction zone as a carbonyl or hydrocarbonyl derivative. Here, suitable examples include tetrarhodium dodecacarbonyl, dirhodium octacarbonyl, hexarhodium hexadecacarbonyl ($Rh_6(CO)_{16}$), rhodium tetracarbonyl salts, and substituted carbonyl species such as rhodium dicarbonyl acetylacetonate.

Rhodium complexes containing Group VB donor ligands such as triphenylphosphine may be effective catalyst precursors under certain conditions.

Preferred rhodium-containing compounds include oxides of rhodium, rhodium salts of a mineral acid, rhodium salts of organic carboxylic acids and rhodium carbonyl or hydrocarbonyl derivatives. Among these, particularly preferred are rhodium(III) chloride, rhodium(III) acetylacetonate, rhodium sesquioxide ($Rh_2O_3$), rhodium dicarbonyl acetylacetonate, rhodium(II) acetate, rhodium(II) propionate, and hexarhodium hexadecacarbonyl.

The iodide or bromide promoter found necessary to effect the desired acid homologation reaction may be in combined form with the rhodium, as for instance in rhodium(III) iodide and $Rh(CO)_3I_2$, but it is generally preferred to have an excess of halogen present in the catalyst system as a promoting agent. By excess is meant an amount of halogen greater than three atoms of halogen per atom of rhodium in the catalyst system. This promoting component of the catalyst system may consist of a halogen, and/or a halogen compound, that may be introduced into the reaction zone in a gaseous or liquid form, or saturated in a suitable solvent or reactant. Satisfactory halogen promoters include hydrogen halides, such as hydrogen iodide, hydriodic acid, alkyl and aryl halides containing 1 to 12 carbon atoms such as methyl iodide, ethyl iodide, 1-iodopropane, 2-iodobutane, 1-iodobutane, ethyl bromide, iodobenzene and benzyl iodide as well as acyl iodides such as acetyl iodide. Also suitable as halogen prompters are the quaternary ammonium and phosphonium halides; examples include tetramethylammonium iodide and tetrabutylphosphonium iodide. Alkali and alkaline earth halides, such as cesium iodide, may also be used but are generally not as effective as other listed promoters for this homologation.

The lower alkyl iodide or bromide promoters containing 1-6 carbon atoms are the preferred promoters for the rhodium-catalyzed acid homologation reaction of this invention. Most preferred are methyl iodide and ethyl iodide.

Starting carboxylic acids useful in the process of this invention are aliphatic acids containing 2-6 carbon atoms. Preferably, said acids are also useful as solvents for the rhodium catalysts. Suitable carboxylic acids include acetic, propionic, butyric, isobutyric, valeric, trimethylacetic, and caproic, together with dialiphatic acids of 2 to 6 carbon atoms, such as oxalic, malonic, succinic and adipic acids. The invention further contemplates the use of substituted monoaliphatic acids containing one or more functional substituents, such as the lower alkoxy, chloro, fluoro, cyano, alkylthio, and amino functional groups, examples of which include acetoacetic acid, dichloroacetic and chloropropionic acid, trichloroacetic acid, monofluoroacetic acid and the like. Mixtures of said carboxylic acids, in any ratio, may also be used in the inventive process. The preferred carboxylic acids homologized here are acetic acid and propionic acid, with acetic acid being most preferred.

The quantity of rhodium catalyst employed in the instant invention is not critical and may vary over a wide range. In general, the novel process is desirably conducted in the presence of a catalytically effective quantity of one or more of the active rhodium species which gives the desired products in reasonable yields. The reaction proceeds when employing as little as about $1 \times 10^{-6}$ weight percent and even lesser amounts of rhodium, basis the total weight of the reaction mixture. The upper concentration is dictated by a variety of factors including catalyst cost, partial pressures of carbon monoxide and hydrogen, operating temperature and choice of carboxylic acid diluent/reactant. A rhodium catalyst concentration of from about $1 \times 10^{-5}$ to about 10 weight percent rhodium, based on the total weight of reaction mixture, is generally desirable in the practice of this invention.

The temperature range which can usefully be employed in these syntheses is a variable dependent upon other experimental factors, including the choice of carboxylic acid co-reactant, the pressure, and the concentration and choice of particular species of rhodium catalyst among other things. The range of operability is from about 100° to about 350° C. when superatmospheric pressures of syngas are employed. A narrower range of about 180° to about 250° C. represents the preferred temperature range.

Superatmospheric pressures of 500 psi or greater lead to substantial yields of desirable aliphatic carboxylic acid higher homologues by the process of this invention. A preferred operating range is from about 1000 psi to about 7500 psi, although pressures above 7500 psi also provide useful yields of the desired acid. The pressures referred to here represent the total pressure generated by all the reactants, although they are substantially due to the carbon monoxide and hydrogen fractions in these examples.

The relative amounts of carbon monoxide and hydrogen which may be initially present in the syngas mixture are variable, and these amounts may be varied over a wide range. In general, the mole ratio of $CO:H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

In all these syntheses in order to achieve a high degree of selectivity the amount of carbon monoxide and hydrogen present in the reaction mixture should be sufficient to at least satisfy the stoichiometry of eq (1). Excess carbon monoxide and/or hydrogen over the stoichiometric amounts may be present, if desired.

As far as can be determined, without limiting the invention thereby, the rhodium-catalyst one-step acid homologation process disclosed herein leads to the formation of acid products primarily containing one carbon atom more than the starting material. Minor amounts of higher acid homologues containing two or three additional carbons are also usually present. In the case then where acetic acid is the co-reactant, the principal products are propionic acid, butyric acid and valeric acid. By-products such as water and ethyl acetate are also detected in the liquid product fraction. Where propionic acid is the reactant acid, the principal products are n-butyric acid and iso-butyric acid. The ratio of isomeric n to iso acids is commonly about 3:1.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired ester product, and said material may be recovered by methods well known in the art, such as distillation, fractionation, extraction and the like. A fraction rich in rhodium catalyst components may then be recycled to the reaction zone, if desired, and additional products generated.

The products have been identified in this work by one or more of the following analytical procedures, viz, gas-liquid phase chromatography (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psi).

The following examples which illustrate various embodiments of the invention are to be considered not limitative.

EXAMPLE I

To a $N_2$-flushed liquid mix of acetic acid (50 g) and methyl iodide (5.67 g., 40 mmole) set in a glass-liner there was added 0.50 g of rhodium(III) oxide (4.0 mmole Rh). The mixture was stirred to partially dissolve the rhodium, and the glass liner plus contents were charged to a 450 ml rocking autoclave. The reactor was flushed with a gaseous mixture containing equal molar amounts of carbon monoxide and hydrogen, pressured to 2000 psi with the same gaseous mixture and heated with rocking to 220° C. At temperature, the pressure was further raised to 6300 psi using the gaseous carbon monoxide/hydrogen mixture and held constant throughout the remainder of the run by incremental addition of the gaseous mixture from a large surge tank.

Upon cooling, depressuring the reactor and sampling of the off-gas, 62.9 g of clear, deep-red liquid product was recovered from the glass liner. Analysis by glc showed the presence of:
29.1% propionic acid
14.7% butyric acid
3.0% valeric acid
4.0% water
47.2% unreacted acetic acid Typical off-gas samples showed the presence of:
27.3% carbon monoxide
35.1% hydrogen
30.8% carbon dioxide
2.8% methane

EXAMPLE 2-5

Following the general procedure of Example 1, additional catalysts and promoters were employed, in Examples 2 to 5. Specifically:
(a) Examples 2 and 4 demonstrate the effective use of methyl iodide with rhodium(III) acetylacetonate $(Rh(AcAc)_3)$ catalyst.
(b) Rhodium(III) chloride was successfully employed as the soluble catalyst in Examples 3 and 5.

Results are summarized in Table I which follows.

EXAMPLES A-H

Following the general procedure of Examples 1–5 inclusive a number of runs were carried out using a variety of additional catalysts with methyl iodide as the promoter and with acetic acid as the starting carboxylic acid. The results which are summarized in Table 1 below show that cobalt, iron, manganese, rhenium, molybdenum and chromium catalysts are ineffective in the homologation of acetic acid to the higher carboxylic acids.

TABLE 1

| Run | Catalyst | Promoter | Aliphatic Acid | $H_2O$ | HOAc | HOPr | HOBu Iso | HOBu n | HOVa tert | HOVa iso | HOVa n |
|---|---|---|---|---|---|---|---|---|---|---|---|
| $1_{a, g}$ | $Rh_2O_3$ | —10 MeI | HOAc | 4.4 | 47.2 | 29.1 | 6.2 | 8.5 | 1.9 | 1.1 | |
| $2_{b, g}$ | $Rh(AcAc)_3$ | —20 MeI | HOAc | 3.7 | 33.2 | 30.2 | 8.9 | 11.1 | 1.1 | 3.0 | 2.7 |
| $3_{b, g}$ | $RhCl_3$ | —20 MeI | HOAc | 4.0 | 42.6 | 29.2 | 7.7 | 8.6 | | 0.7 | 1.6 |
| $4_{b, h}$ | $Rh(AcAc)_3$ | —20 MeI | HOAc | 2.9 | 60.8 | 24.1 | 2.6 | 3.6 | | 0.4 | 0.3 |
| $5_{b, h}$ | $RhCl_3$ | —20 MeI | HOAc | 3.7 | 52.1 | 29.3 | 3.8 | 3.7 | | 0.3 | |
| $A_{c, c}$ | $K_2PtCl_4$—$3PPh_3$ | —28 MeI | HOAc | 5.1 | 80.1 | | | | | | |
| $B_{d, e}$ | $CoI_2$ | —10 MeI | HOAc | 2.4 | 95.4 | | | | | | |
| $C_{d, e}$ | $Co_2(CO)_8$ | — 5 MeI | HOAc | 3.9 | 90.1 | | | | | | |
| $D_{d, e}$ | $Fe(AcAc)_3$ | —10 MeI | HOAc | 2.3 | 95.2 | | | | | | |
| $E_{d, e}$ | $Mn_2(CO)_{10}$ | — 5 MeI | HOAc | 0.5 | 97.8 | | | | | | |
| $F_{d, e}$ | $Re_2(CO)_{10}$ | — 5 MeI | HOAc | 0.7 | 97.5 | | | | | | |
| $G_{a, e}$ | $Mo(AcAc)_3$ | —10 MeI | HOAc | 1.1 | 93.6 | 0.2 | | | | 0.1 | 0.1 |

TABLE 1-continued

| | | | Aliphatic | | | | HOBu | | HOVa | | |
| Run | Catalyst | Promoter | Acid | H₂O | HOAc | HOPr | Iso | n | tert | iso | n |
|---|---|---|---|---|---|---|---|---|---|---|---|
| H<sub>a e</sub> | Cr(AcAc)₃ | —10 MeI | HOAc | 5.4 | 89.7 | | 0.5 | | | 0.6 | 0.2 |

<sub>a</sub>Run Charge: Aliphatic Acid, 50g; Iodide Promoter, 40 mmole; Catalyst, 4.0 mmole.
<sub>b</sub>Run Charge: Aliphatic Acid, 50g; Iodide Promoter, 40 mmole; Catalyst, 2.0 mmole.
<sub>c</sub>Run Charge: Aliphatic Acid, 50g; Iodide Promoter, 112 mmole; Catalyst, 4.0 mmole.
<sub>d</sub>Run Charge: Aliphatic Acid, 50g; Iodide Promoter, 20 mmole; Catalyst, 4.0 mmole.
<sub>e</sub>Run Conditions: Initial pressure 4000 psi of CO/H₂ (1:1), 220° C., 18 hr.
<sub>f</sub>Designations: Propionic acid, HOPr; Butyric Acid, HOBu; and Valeric acid, HOVa.
<sub>g</sub>Run Conditions: Constant Pressure 6300 psi of CO/H₂ (1:1), 220° C., 18 hr.
<sub>h</sub>Run Conditions: Constant Pressure 6300 psi of CO/H₂ (1:1), 220° C., 6 hr.

What is claimed is:

1. A process of preparing higher homologues of aliphatic carboxylic acids containing 2–6 carbon atoms which comprises the steps of contacting said aliphatic carboxylic acid starting material with at least a catalytic amount of a rhodium-containing compound in the presence of an iodide or bromide promoter and heating the resultant reaction mixture at a temperature of from about 100° to about 350° C. and under super-atmospheric pressures of 500 psi or greater with carbon monoxide and hydrogen until substantial formation of the desired acids containing at least three (3) carbon atoms has been achieved, and recovering said desired acids.

2. The process of claim 1 wherein the said reaction mixture is heated at a temperature of about 180° to about 250° C.

3. The process of claim 1 wherein the process is conducted at a pressure of about 1000 psi to about 7500 psi.

4. The process of claim 1 wherein the rhodium-containing compound is selected from the group consisting of one or more oxides of rhodium, rhodium salts of a mineral acid, rhodium salts of an organic carboxylic acid and rhodium carbonyl or hydrocarbonyl derivatives.

5. The process of claim 1 wherein the rhodium-containing compound is selected from the group consisting of rhodium(III) chloride, rhodium sesquioxide, rhodium(III) acetylacetonate, rhodium dicarbonyl acetylacetonate, rhodium (II) acetate, rhodium(II) propionate, and hexarhodium hexadecacarbonyl.

6. The process of claim 1 wherein said iodide or bromide promoter is an alkyl iodide or bromide containing 1–6 carbon atoms.

7. The process of claim 6 wherein said promoter is selected from the group consisting of methyl iodide, methyl bromide, ethyl iodide and ethyl bromide.

8. The process of claim 1 wherein said aliphatic carboxylic acid starting material is acetic acid.

9. The process of claim 1 wherein said rhodium-containing catalyst is rhodium sesquioxide.

10. The process of claim 1 wherein said rhodium-containing catalyst is rhodium(III) chloride.

11. The process of claim 1 wherein said rhodium-containing catalyst is rhodium(III) acetylacetonate.

12. The process of claim 1 wherein the said aliphatic acid starting material is acetic acid, the said promoter is methyl iodide and the said catalyst is rhodium sesquioxide.

13. The process of claim 1 wherein the said aliphatic carboxylic acid starting material is acetic acid, the said promoter is methyl iodide and the said catalyst is rhodium(III) chloride.

14. The process of claim 1 wherein the said aliphatic carboxylic acid starting material is acetic acid, the said promoter is methyl iodide and the said catalyst is rhodium(III) acetylacetonate.

* * * * *